(12) United States Patent
Kim et al.

(10) Patent No.: US 10,562,911 B2
(45) Date of Patent: Feb. 18, 2020

(54) METHOD FOR ISOLATING FLAVONOIDS FROM RICE PLANT INOCULATED WITH WHITEBACKED PLANTHOPPER

(71) Applicant: Kyung Min Kim, Daegu (KR)

(72) Inventors: Kyung Min Kim, Daegu (KR); Byung Wook Yun, Daegu (KR)

(73) Assignee: Kyung Min Kim, Daegu (KR)

( * ) Notice: Subject to any disclaimer, the term of this patent is extended or adjusted under 35 U.S.C. 154(b) by 204 days.

(21) Appl. No.: 15/714,607

(22) Filed: Sep. 25, 2017

(65) Prior Publication Data

US 2018/0086773 A1 Mar. 29, 2018

Related U.S. Application Data

(63) Continuation-in-part of application No. PCT/KR2016/000952, filed on Jan. 28, 2016, and a continuation-in-part of application No. PCT/KR2016/000950, filed on Jan. 28, 2016.

(30) Foreign Application Priority Data

Mar. 24, 2015 (KR) .................. 10-2015-0040915
Mar. 24, 2015 (KR) .................. 10-2015-0040924

(51) Int. Cl.
*C07D 493/04* (2006.01)
*C07D 311/40* (2006.01)
*A01H 5/10* (2018.01)

(52) U.S. Cl.
CPC ........... *C07D 493/04* (2013.01); *A01H 5/10* (2013.01); *C07D 311/40* (2013.01)

(58) Field of Classification Search
CPC ................. C07D 311/40; A01H 5/10
See application file for complete search history.

(56) References Cited

FOREIGN PATENT DOCUMENTS

| JP | H07149637 A | 6/1995 |
|---|---|---|
| KR | 10-2012-0089893 A | 8/2012 |

OTHER PUBLICATIONS

Park, Seul Gi, Graduate School of Kyungpook National University, Master's Thesis, Aug. 2014 (Year: 2014).*
Dong, Xuekui, et al. "Comprehensive profiling and natural variation of flavonoids in rice." Journal of integrative plant biology 56.9 (2014): 876-886. (Year: 2014).*
Duan, Canxing, et al. "Induced defense responses in rice plants against small brown planthopper infestation." The Crop Journal 2.1 (2014): 55-62. (Year: 2014).*
Park et al., "Analysis of QTL Associated with WBPH and Identification of WBPH Mediated Compounds in Rice (*Oryza sativa* L.)", Thesis for the degree of Master of Agriculture, 2014, pp. 1-34.
Miyagawa et al., "Phytotoxins Produced by the Plant Pathogenic Fungus Bipolar is bicolor EI-1", Bioscience, Biotechnology, and Biochemistry, 1994, vol. 58, No. 6, pp. 1143-1145.
Ogo et al., "Transgenic rice seed synthesizing diverse flavonoids at high levels: a new platform for flavonoid production with associated health benefits", Plant Biotechnology Journal, 2013, vol. 11, pp. 734-746.
Park et al., "Analysis of QTL Associated with WBPH and Identification of WBPH Mediated Compounds in Rice (*Oryza Sativa* L.)", The Korean Society of Breeding Science, 2014, vol. 46, No. 1, pp. 132.
Schaeffer et al., "Cochlioquinone A, A Nematocidal Agent Which Competers for Specific [3H] Invermectin Binding Sites", The Journal of Antibiotics, 1990, vol. XLIII, No. 9, pp. 1179-1182.
Phuwapraisirisan et al., "Anhydrocochlioquinone A, a new antitumor compound from *Bipolaris oryzae*" Tetrahedron Letters 48, 2007, pp. 5193-5195.

* cited by examiner

*Primary Examiner* — Weihua Fan
(74) *Attorney, Agent, or Firm* — Lucas & Mercanti, LLP

(57) ABSTRACT

The present invention relates to a method for isolating flavonoids such as cochlioquinone or chrysoeriol from a rice plant inoculated with a whitebacked planthopper. The method of the present invention, for example, facilitates not only the fast production of flavonoids such as cochlioquinone or chrysoeriol but also the mass-production of flavonoids such as cochlioquinone or chrysoeriol with high efficiency in addition to the advantage of saving costs. Therefore the method of the present invention can be effectively used for the production of flavonoids such as cochlioquinone or chrysoeriol and also be used in various fields using the same.

8 Claims, 5 Drawing Sheets

Figure 1A
Figure 1B
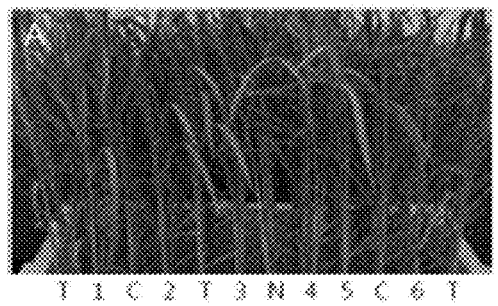
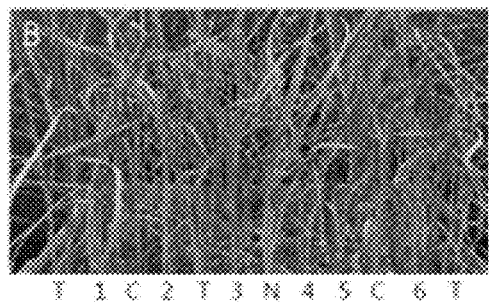
Figure 2
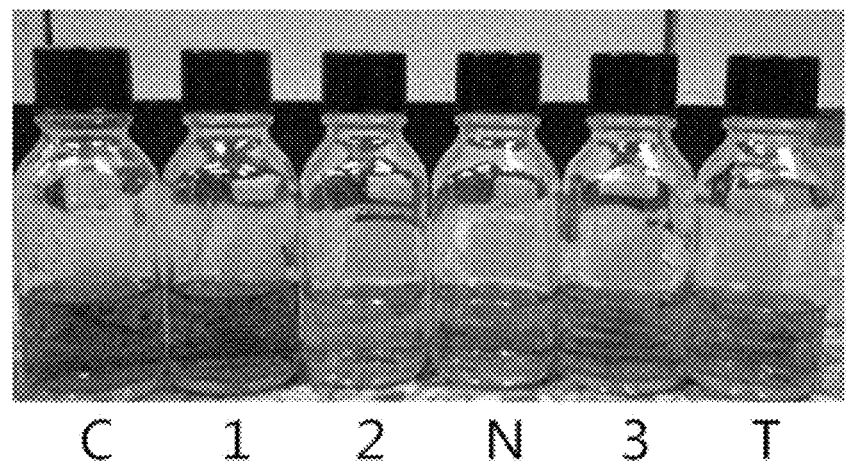

METHOD FOR ISOLATING FLAVONOIDS FROM RICE PLANT INOCULATED WITH WHITEBACKED PLANTHOPPER

CROSS-REFERENCE TO RELATED APPLICATIONS

This application is a continuation-in-part of PCT/KR2016/000950 filed Jan. 28, 2016, which claims the benefit of priority from Korean Application No. 10-2015-0040924 filed Mar. 24, 2015, the contents of each of which are incorporated herein by reference.

This application is also a continuation-in-part of PCT/KR2016/000952 filed Jan. 28, 2016, which claims the benefit of priority from Korean Application No. 10-2015-0040915 filed Mar. 24, 2015, the contents of each of which are incorporated herein by reference.

FIELD OF THE INVENTION

The present invention relates to a method for isolating flavonoids including cochlioquinone and chrysoeriol from rice plant inoculated with whitebacked planthopper.

BACKGROUND OF THE INVENTION

Planthopper is an insect belonging to Delphacidae, and 1800 species of which have been identified so far. The body is 2~9 mm long and it has a short head. It has simple antennas and short front wings. The wing vein is degenerated. It has movable spinous processes at the end of the hind leg calf segment. The planthopper lives on various plants and both adults and larvae are harmful to crops such as rice, barley, corn, and sugar cane. Many adults and larvae secrete white waxy materials from the abdomen or back of the body. The adults that are active in winter can be observed in the southern part of Korea and in the islands of southern sea. The planthopper is distributed world-widely basically along the tropical area. In Korea, 33 species of the planthopper including brown planthopper, whitebacked planthopper, and small brown planthopper are distributed.

Among them, the whitebacked planthopper has a dark brown body and the female has a brighter colored body than the male. It has a long grayish yellow pattern in the middle of the waist. This insect is harmful to rice and barley by carrying dwarf to them. Like the brown planthopper, the whitebacked planthopper cannot stay over winter in Korea and flies from the southern part of China every year. The population of the whitebacked planthopper flying over from China is 10 times larger than the brown planthopper but the damage is not focused on a certain area but spread instead, which seems less serious. The life of one generation of the whitebacked planthopper is about 24 days at 25° C., more precisely, the before spawning period is 4.6 days, the spawning period is 7.6 days, and the spawning period is 13 days. In the outdoor temperature between June and August, it spends one generation in 20~30 days. The life span of the adult is 15.6 days, the number of eggs is about 250, and the egg lay on the leaf sheath. The adult lays about 250 eggs in a pile on a plant leaf.

Flavonoids are a class of plant and fungus secondary metabolites. Chemically, flavonoids have the general structure of a 15-carbon skeleton, which consists of two phenyl rings (A and B) and heterocyclic ring (C).

Cochlioquinone ($C_{30}H_{44}O_8$) is one of the flavonoids and is the main component of the living pigments isolated from Bipolarisleersia. It is known that cochlioquinone can be used as an antagonist of the human chemokine receptor CCR5 in human immunodeficiency virus type 1 (HIV-1). Cochlioquinone has been confirmed to have the activity of anti-angiogenesis and to inhibit diacylglycerol acyltransferase and NADH ubiquinone reductase.

Chrysoeriol ($C_{16}H_{12}O_6$) is one of the flavonoids and is a component mainly contained in Eriodyctionglutinosum Bentham leaves. It is a yellow needle like crystal and is melted at 337° C. It is hardly dissolved in ethyl acetate and ethanol, but is easily melted in hot pyridine. Chrysoeriol is known to have the activity of lowering lipid concentration.

There are many methods for the separation or isolation of cochlioquinone and chrysoeriol reported so far but they cost a lot and the production efficiency is very low. Therefore, it is requested to develop a novel separation method.

SUMMARY OF THE INVENTION

The present invention provides a method for isolating flavonoids including cochlioquinone and chrysoeriol from rice plant inoculated with whitebacked planthopper.

One aspect of the present invention provides a method for increasing the content of cochlioquinone or chrysoeriol in a rice extract containing the step of inoculating rice seeds with a planthopper and a method for enhancing the efficiency of isolating cochlioquinone or chrysoeriol from the rice extract.

Another aspect of the present invention provides a method for isolating cochlioquinone or chrysoeriol from a rice extract comprising the following steps:

(a) inoculating rice seeds with a planthopper; and (b) isolating cochlioquinone or chrysoeriol from the obtained rice extract after germinating and growing the rice seeds of step (a).

BRIEF DESCRIPTION OF THE DRAWINGS

FIG. 1 is a diagram illustrating the rice not-inoculated with the whitebacked planthopper (FIG. 1A) and the rice inoculated with the whitebacked planthopper (FIG. 1B). [T: TN1, N: Nagdong, C: Cheongcheong, 1-6: CNDH]

FIG. 2 is a diagram illustrating the rice extract obtained from the rice inoculated with the whitebacked planthopper. [T: TN1, N: Nagdong, C: Cheongcheong, 1-3: CNDH]

DETAILED DESCRIPTION OF THE INVENTION

Figure 3A:
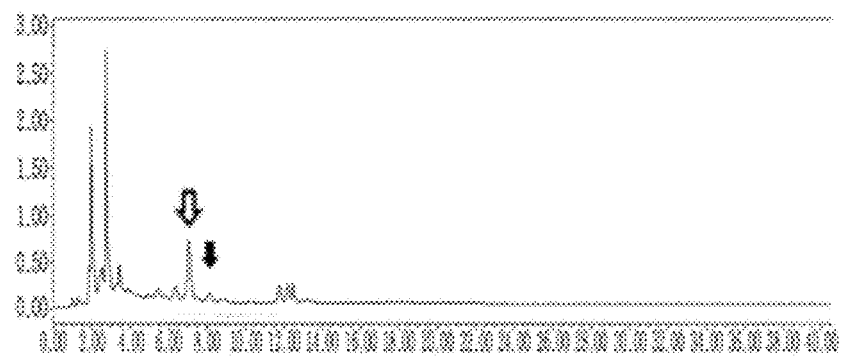
FIGS. 3A~3F are diagrams illustrating the results of HPLC with the rice extract obtained from the rice inoculated with the whitebacked planthopper. [A: control Cheongcheong, B: control Nagdong, C: treated Cheongcheong, D: treated Nagdong, E: treated CNDH 115, F: treated CNDH 52] [⇩ cochlioquinone; ✦ chrysoeriol]
Figure 3B:
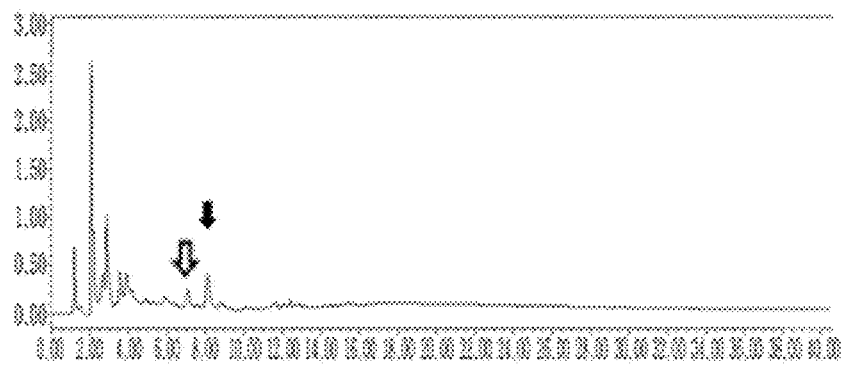
Figure 3C:
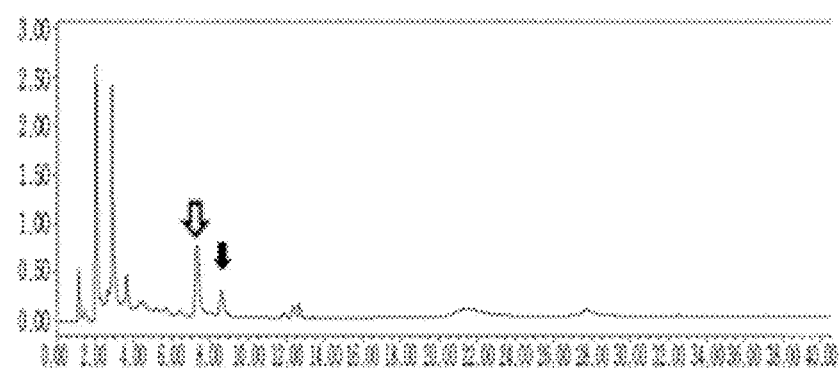
Figure 3D:
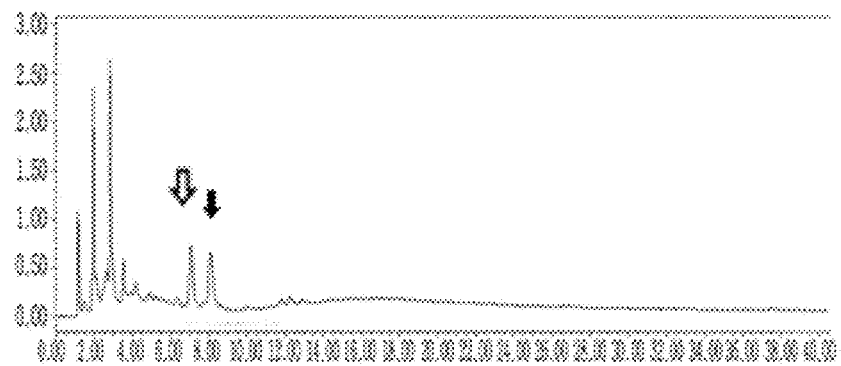
Figure 3E:
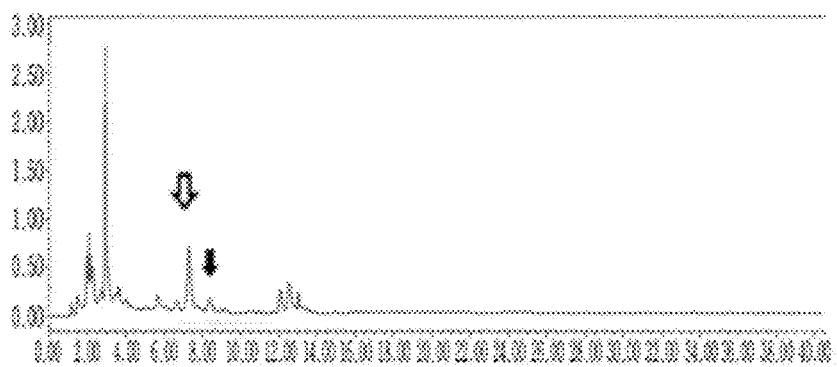
Figure 3F:
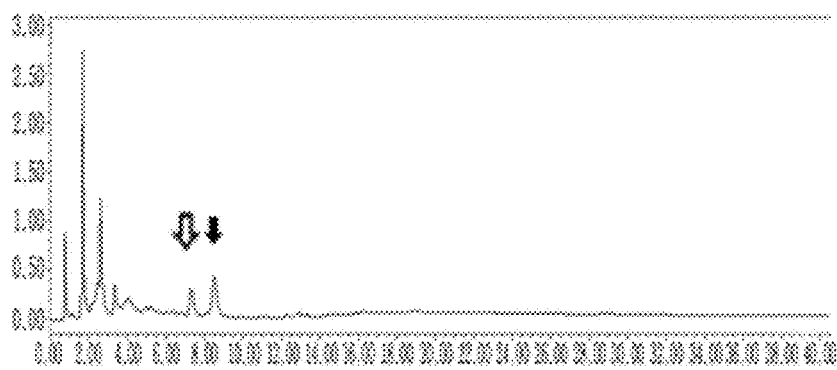

The present invention provides a method for isolating flavonoids including cochlioquinone and chrysoeriol from rice plant inoculated with whitebacked planthopper.

One aspect of the present invention provides a method for increasing the content of cochlioquinone or chrysoeriol in a rice extract containing the step of inoculating rice seeds with a planthopper and a method for enhancing the efficiency of isolating cochlioquinone or chrysoeriol from the rice extract.

Another aspect of the present invention provides a method for isolating cochlioquinone or chrysoeriol from a rice extract comprising the following steps:

(a) inoculating rice seeds with a planthopper; and
(b) isolating cochlioquinone or chrysoeriol from the obtained rice extract after germinating and growing the rice seeds of step (a).

Cochlioquinone ($C_{30}H_{44}O_8$) of the present invention is a kind of flavonoids, which is represented by the Chemical Formula 1 below and is (3R)-9-[(1S,2R,3S)-2-Acetyloxy-1,3-dimethylpentyl]-1,2,3,4a,5,6,6a,12,12a,12b-decahydro-12-hydroxy-3-(1-hydroxy-1-methylethyl)-6a,12b-dimethyl-pyrano[3,2-a]xanthene-8,11-dione.

[Chemical Formula 1]

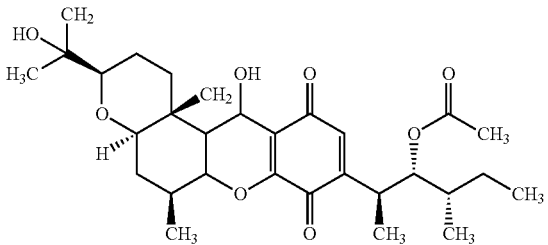

Chrysoeriol ($C_{16}H_{12}O_6$) of the present invention is a kind of flavonoids, which is represented by the Chemical Formula 2 below and is 5,7-dihydroxy-2-(4-hydroxy-3-methoxyphenyl)chromen-4-one.

[Chemical Formula 2]

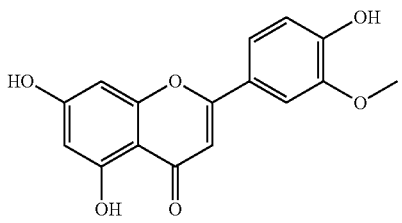

Step (a) above is inoculating rice seeds with the planthopper, wherein the planthopper is an insect belonging to Delphacidae including whitebacked planthopper, brown planthopper, and small brown planthopper, but not always limited thereto, but preferably whitebacked planthopper (Sogatellafurcifera).

Rice seeds above are preferably obtained by cultivating Cheongcheong, Nagdong, Cheongcheong/Nagdong haploid, or Taichung Native No. 1 (TN1) seeds, but not always limited thereto. In this present invention, the seeds obtained by hybridization with Cheongcheong and Nagdong were used. Cheongcheong is resistant to the whitebacked planthopper, Nagdong is good in taste, and TN1 is known to be sensitive to the whitebacked planthopper.

The germination of step (b) is the step of budding before seeding rice seeds, which can be performed at 26~34° C. for 5~9 days. The germination can be carried out in a greenhouse.

In step (b), the rice plant grows at 26~28° C. with 60~70% humidity, during which the duration of sunshine preferably maintains as 11~13 hours a day.

In step (b), a rice extract is prepared, from which cochlioquinone or chrysoeriol is isolated. The rice extract above can be obtained from rice using water, $C_1$~$C_4$ alcohol or a mixture thereof as an extraction solvent. Preferably, methanol is used as a solvent herein.

In step (b), an additional step of eliminating fat from the rice extract and drying thereof can be included before the isolation of cochlioquinone or chrysoeriol.

The fat can be eliminated by using an organic solvent which is one or more solvents preferably selected from the group consisting of ether, chloroform, acetone, benzene, and hexane.

The isolation herein can be performed by using a mixed solvent comprising chloroform, methanol, butanol, and water, wherein the ratio of chloroform:methanol:butanol:water is preferably 4:5:6:4 (v/v), but not always limited thereto.

The isolation can be performed by using a mixed solvent comprising chloroform, methanol, butanol, and water, wherein the volume of methanol is preferably 10-60% (v/v), 20-50% (v/v), or 20-40% (v/v), but not always limited thereto.

The method for isolating cochlioquinone or chrysoeriol from the rice plant inoculated with the planthopper of the present invention facilitates not only the fast production of cochlioquinone or chrysoeriol but also the mass-production thereof with a high efficiency in addition to the cost saving effect. Therefore, the method can be effectively used for the production of cochlioquinone or chrysoeriol and also in various fields using the same.

The present invention provides a method for increasing the content of cochlioquinone or chrysoeriol in a rice extract containing the step of inoculating rice seeds with a planthopper and a method for enhancing the efficiency of isolating cochlioquinone or chrysoeriol from the rice extract.

The present invention also provides a rice plant with increased cochlioquinone or chrysoeriol content by being inoculated with a planthopper.

The present invention also provides the cochlioquinone or chrysoeriol prepared by the isolation method above.

The numerical values described in this invention are to be understood as including equivalent ranges unless stated otherwise.

EXAMPLES

Practical and presently preferred embodiments of the present invention are illustrative as shown in the following Examples, but not limited by the following examples, for the better understanding of several aspects of the present invention.

Example 1: Plant Material and Biological Examination

Whitebacked planthopper (WBPH) was raised in an acryl growth box (50×50×40 cm). The growth chamber was maintained at the temperature of 27° C. with the humidity of 60~70% and the sunshine condition was maintained for 16 hours a day at the light strength of 3,000 lux. 40~50 pairs of WBPHs were raised and crossed in that box. Chucheongbyeo (20~25 g) was given as feeds which was washed with running water after sterilization and then sprouted at 29~30° C. for 7 days, followed by germination in a greenhouse. Young rice plants which had grown for 10 days were replaced every 3~4 days as fresh feeds.

When the planthoppers were 2~3 instar, they were inoculated to 120 Cheongcheong (indica)/Nagdong (japonica) haploid (CNDH), Cheongcheong, Nagdong, and TN1 seeds harvested at Kyungpook National University Farm in 2012 for 3 weeks. After the inoculation, 30~35 seeds of each line were soaked in disinfectant for 24 hours, followed by washing with running water. The seeds were sprouted at 29~30° C. for 6 days in the darkness. The sprouted seeds were arranged in 12 rows with 0.8 cm (3 cm between each line) intervals and each row contained 20 seeds, which were planted in a 5 cm deep box (32×23×10 cm). This plantation repeated twice for each line. Light was given in the greenhouse at the strength of 3,000 lux for 12±1. The seeds were grown at the temperature of 26~28° C. with the humidity of 60~70%. The results are shown in FIG. 1.

As shown in FIG. 1, all lines of seeds that had not been treated with the whitebacked planthopper grew well. Among the seeds treated with the whitebacked planthopper, Cheongcheong displaying the resistance against the whitebacked planthopper turned blue, while the leaves and stems of Nagdong and TN1 which did not show the resistance were dried. Some of CNDH showed the resistance against the whitebacked planthopper like Cheongcheong.

Example 2: Rice Extract and Analysis Thereof

The upper part of the rice inoculated with the whitebacked planthopper in example 1 and the uninoculated rice was cut out and 5 g of leaves and stems were ground by using liquid nitrogen. The powders were added with 90% methanol, followed by extraction. The process is shown in FIG. 2.

The methanol solution above was loaded in a 50 ml falcon tube, followed by reaction in the darkness for 3 days at room temperature. Then, the solution was further reacted in a sonicator at 24±1° C. for 20 minutes. Lipid was separated therefrom by using nucleic acid. The remaining solution was evaporated by using an evaporator. 1 g of the dried sample was dissolved in 1 ml of methanol for HPLC, and then filtered with 0.45 ml filter to obtain a sample for HPLC. The prepared sample was loaded in reverse-phase HPLC column (ZORBAX 4.625010 mm, particle size 5 mm Agilent, USA), on which acetonitrile solution (A) and 1% acetic acid solution (B) were spilled at the speed of 1 ml/min for 50 minutes. HPLC was performed by using UV 254 nm detector (1525 pump, 2487 detector and 717 plus autosampler, Waters). The results are shown in FIG. 3.

As shown in FIGS. 3A~3F and 8A~8F, CNDH displayed different concentrations among them and the arrow indicates cochlioquinone or chrysoeriol. The treatment of the whitebacked planthopper changed the phenomenon, compared with the treatment was not applied.

As shown in FIG. 3, CNDH displayed different concentrations among them and the arrow indicates cochlioquinone or chrysoeriol. The treatment of the whitebacked planthopper changed the phenomenon, compared with the treatment was not applied.

[⬇ cochlioquinone; ⬇ chrysoeriol]

These results were different when planthopper was treated and not treated.

Figure 4:
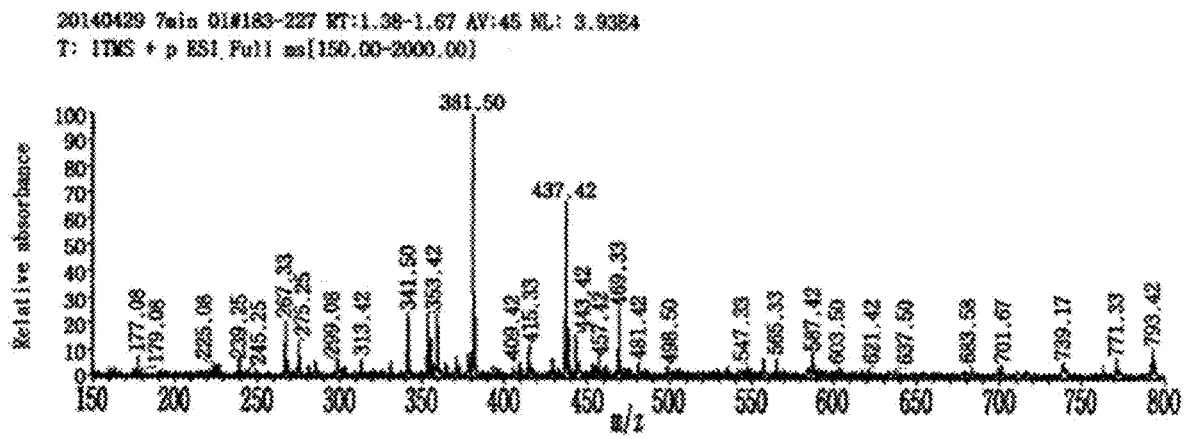
FIG. 4 is a diagram illustrating the results of LC/MS with the rice extract obtained from the rice inoculated with the whitebacked planthopper.

As shown in FIG. 4, for the LC/MS analysis of cochlioquinone or chrysoeriol, the sample was diluted at the concentration of 1000 ppm, on which 50% methanol and 0.1% formic acid (50 μl/min) were spilled at 320° C. with 49V electrode.

The molecular weights of the cochlioquinone positive control and the negative control were respectively 381.50 and 469.42 m/z. The molecular weights of the chrysoeriol positive control and the negative control were respectively 267.33, 341.50, 353.42, and 381.50 m/z.

As shown in FIG. 4, cochlioquinone and chrysoeriol, the compounds of the present invention, were confirmed to have a structure with glycoside attached to flavonoid and quinine.

Example 3: QTLs Analysis

QTLs analysis with the rice extract prepared in example 2 was performed by using WinQTLcart2.5 version program. This program is useful for identifying the location and information of a gene by using the distance between the marker genes in chromosome. Composite interval mapping (CIM) was set on LOD 2.5 of WinQTLcart2.5 program and the concentration values of peak A and peak B of each line compound were applied thereto. The results are shown in Table 1.

TABLE 1

| QLT | Marker | Chr.[a] | LOD[b] | Variation (%) | Add.[c] |
|---|---|---|---|---|---|
| cochlioquinone | | | | | |
| qFla8 | RM23230-RM3689 | 8 | 2.5 | 30 | −1.5 |
| chrysoeriol | | | | | |
| qFla4 | RM280-RM6909 | 4 | 3.5 | 30 | 1.1 |
| qFla7 | RM248-RM1134 | 6 | 3.0 | 30 | 1.2 |
| qFla12 | RM1226-RM12 | 12 | 2.7 | 40 | 1.1 |

[a]chromosome,
[b]logarithms,
[c]additive effect

As shown in Table 1, as a result of QTLs analysis with the sample treated with the whitebacked planthopper for 21 days, cochlioquinone was identified at chromosome 8. qFla8 was identified in the position between M23230 and RM3689 at chromosome 8. The rate of variability was 30% and the LOD value was 2.5.

As shown in Table 1, as a result of QTLs analysis with the sample treated with the whitebacked planthopper for 21 days, chrysoeriol was identified at chromosomes 4, 7, and 12. qFla4 was identified in the position between RM280 and RM6909 at chromosome 4. The rate of variability was 30% and the LOD value was 3.0. qFla12 was identified in the position between RM1226 and RM12 at chromosome 12. The rate of variability was 30% and the LOD value was 2.7.

Figure 5:
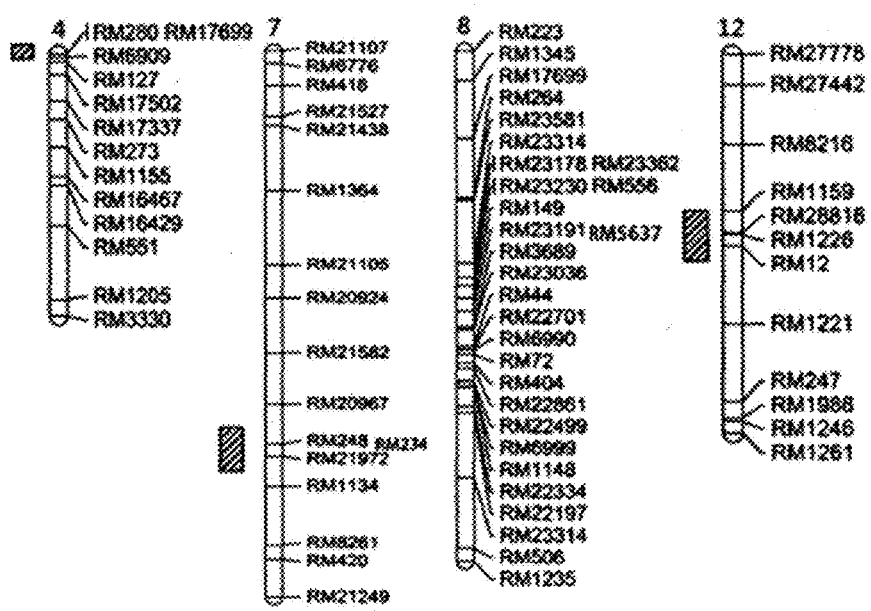
FIG. 5 is a diagram illustrating the chromosomal location of cochlioquinone-related genes according to QTLs analysis with the rice extract obtained from the rice inoculated with the whitebacked planthopper.

The chromosomal gene loci associated with cochlioquinone and chrysoeriol according to the QTLs analysis were identified, which are shown in FIG. 5.

As shown in FIG. 5, qFla8 gene was originated from 'Cheongcheong' and confirmed to be involved in the resistance against the whitebacked planthopper.

As shown in FIG. 5, qFla4, qFla7 and qFla12 genes were originated from 'Nagdong' and confirmed to be involved in the sensitivity.

Example 4: Compound Isolation

The upper part of the rice inoculated with the whitebacked planthopper in example 1 and the uninoculated rice was cut out, followed by grinding using liquid nitrogen. The powders were loaded in a 50 ml falcon tube, followed by extraction with 90% methanol. Fat was eliminated from the extract using nucleic acid, followed by drying. The dried extract was loaded in a column (diameter 10×250 mm) together with silica gel 60F254 (E-Merck). The isolation of a single material was performed by using the solution comprising chloroform:methanol:1-butanol:water at the ratio of 4:5:6:4. The isolated material was analyzed by TLC. At this time, the developing solvent was prepared with chloroform:methanol:1-butanol:water at the ratio of 4:5:6:2. To increase the concentration of the target material, evaporation was induced at 60° C. The results of TLC are shown in FIG. 6.

Figure 6:
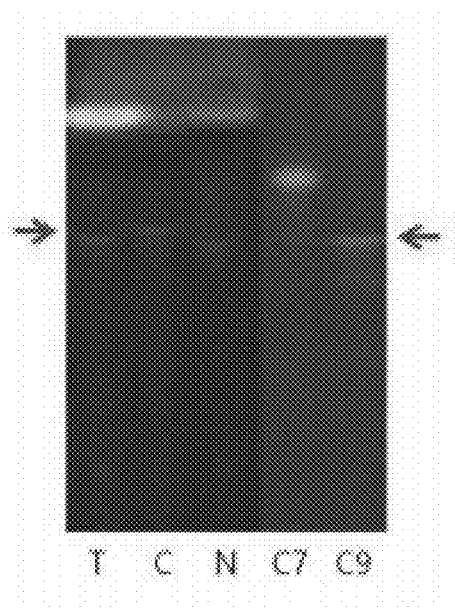
FIG. 6 is a diagram illustrating the separation of cochlioquinone of the invention from the rice extract obtained from the rice inoculated with the whitebacked planthopper, confirmed by TLC.

As shown in FIG. 6, the target material cochlioquinone was isolated. The isolated material was loaded in a brown bottle and stored at 20° C. The isolated compound was cochlioquinone with the mass values of 381.50 m/z and 469.42 m/z.

Figure 7:
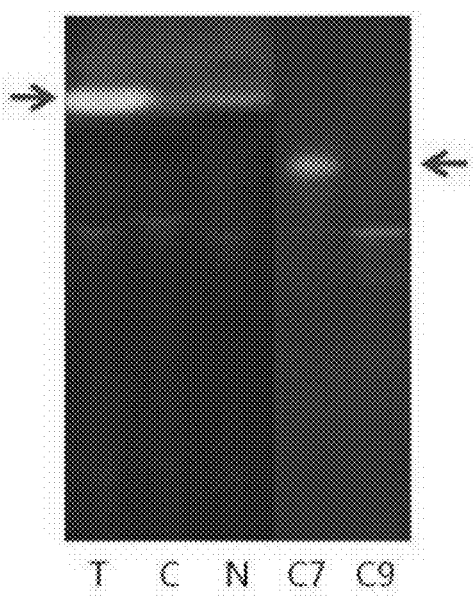
FIG. 7 is a diagram illustrating the separation of chrysoeriol of the invention from the rice extract obtained from the rice inoculated with the whitebacked planthopper, confirmed by TLC.

As shown in FIG. 7, the target material chrysoeriol was isolated. The isolated material was loaded in a brown bottle and stored at 20° C. The isolated compound was chrysoeriol with the mass values of 267.33 m/z, 341.50 m/z, 353.42 m/z, 381.50 m/z, 437.42 m/z, and 469.33 m/z.

Example 5: Efficiency of Compound Isolation

The isolation efficiency of cochlioquinone and chrysoeriol in example 4 was investigated. The results are shown in Table 2.

TABLE 2

| Stage | Line | Cochlioquinone (ng/gram weight) | Efficiency (%) |
|---|---|---|---|
| Vegetative period | Cheongcheong | 7.81 ± 0.29 | 0.0007 |
|  | Nagdong | 5.43 ± 0.21 | 0.0005 |
|  | TN1 | 9.67 ± 1.17 | 0.001 |
| Reproductive growth period | Cheongcheong | 4.91 ± 1.17 | 0.0004 |
|  | Nagdong | 3.28 ± 0.16 | 0.0003 |
| Vegetative period | Cheongcheong | 12.26 ± 0.03a | 0.0012 |
|  | Nagdong | 12.95 ± 0.62 | 0.0013 |
|  | TN1 | 43.34 ± 1.52 | 0.0043 |
| Reproductive growth period | Cheongcheong | 4.04 ± 0.79 | 0.0004 |
|  | Nagdong | 3.75 ± 0.51 | 0.0003 | amean SD.

As shown in Table 2, the isolation efficiency of cochlioquinone and chrysoeriol from the rice plant inoculated with the whitebacked planthopper was confirmed to be very high.

We claim:

1. A method for isolating flavonoids comprising the following steps:
    (a) inoculating rice seeds with a planthopper;
    (b) extracting rice extract from rice obtained after germinating and growing the rice seeds of step (a); and
    (c) isolating flavonoids containing cochlioquinone or chrysoeriol from the rice extract of step (b).

2. The method for isolating flavonoids according to claim 1, wherein the planthopper is the whitebacked planthopper (Sogatellafurcifera).

3. The method for isolating flavonoids according to claim 1, wherein the rice seed is Cheongcheong, Nagdong, Cheongcheong/Nagdong haploid, or Taichung Native No. 1 (TN1).

4. The method for isolating flavonoids according to claim 1, wherein the rice extract is extracted from rice by using water, $C_1$~$C_4$ alcohol or a mixture thereof as a solvent.

5. The method for separating flavonoids according to claim 4, wherein the rice extract is extracted from rice by using methanol.

6. The method for isolating flavonoids according to claim 1, wherein the step (c) includes an additional step of eliminating fat from the rice extract and drying thereof before the isolation of chrysoeriol.

7. The method for isolating flavonoids according to claim 1, wherein the elimination of fat is performed by using one or more organic solvents selected from the group consisting of ether, chloroform, acetone, benzene, and hexane.

8. The method for isolating flavonoids according to claim 1, wherein the isolation is performed by using a mixed solvent composed of chloroform, methanol, butanol, and water.

* * * * *

UNITED STATES PATENT AND TRADEMARK OFFICE
CERTIFICATE OF CORRECTION

| | |
|---|---|
| PATENT NO. | : 10,562,911 B2 |
| APPLICATION NO. | : 15/714607 |
| DATED | : February 18, 2020 |
| INVENTOR(S) | : Kyung Min Kim |

It is certified that error appears in the above-identified patent and that said Letters Patent is hereby corrected as shown below:

On the Title Page

Item (12) delete "Kim et al." and insert -- Kim --

On Column 1, item (72) Inventors should read:
-- Inventor: Kyung Min Kim, Daegu (KR) --

Signed and Sealed this
Eighth Day of August, 2023

Katherine Kelly Vidal
*Director of the United States Patent and Trademark Office*